(12) United States Patent
Patel et al.

(10) Patent No.: US 6,608,011 B2
(45) Date of Patent: Aug. 19, 2003

(54) SHAMPOOS WITH BEHENYL-ALCOHOL

(75) Inventors: Amrit Patel, Dayton, NJ (US);
Raymond Babecki, Fords, NJ (US);
Saurabh Desai, North Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 126 days.

(21) Appl. No.: 09/878,805

(22) Filed: Jun. 11, 2001

(65) Prior Publication Data

US 2003/0130145 A1 Jul. 10, 2003

(51) Int. Cl.$^7$ .............................. C11D 1/12; C11D 9/36
(52) U.S. Cl. .................... 510/124; 510/119; 510/121; 510/122; 510/123; 510/125; 510/127; 510/426; 510/432; 510/433; 510/503; 510/504
(58) Field of Search ................. 510/119, 121, 510/122, 123, 124, 125, 127, 426, 432, 433, 503, 504

(56) References Cited

U.S. PATENT DOCUMENTS

| | | | | |
|---|---|---|---|---|
| 4,000,077 A | | 12/1976 | Wixon | |
| 4,252,787 A | * | 2/1981 | Sherman et al. | 424/45 |
| 4,741,855 A | | 5/1988 | Grote et al. | |
| 4,786,422 A | | 11/1988 | Kern | |
| 4,888,119 A | | 12/1989 | Klewsaat | |
| 4,929,367 A | | 5/1990 | Thomas et al. | |
| 4,997,641 A | | 3/1991 | Hartnett et al. | |
| 5,002,680 A | * | 3/1991 | Schmidt et al. | 252/90 |
| 5,051,250 A | | 9/1991 | Patel et al. | |
| 5,078,991 A | * | 1/1992 | Birtwistle et al. | 424/70 |
| 5,100,657 A | * | 3/1992 | Ansher-Jackson et al. | 424/70 |
| 5,106,613 A | | 4/1992 | Hartnett et al. | |
| 5,213,716 A | | 5/1993 | Patel et al. | |
| 5,275,761 A | * | 1/1994 | Bergmann | 252/551 |
| 5,348,736 A | | 9/1994 | Patel et al. | |
| 5,358,667 A | * | 10/1994 | Bergmann | 252/547 |
| 5,384,114 A | * | 1/1995 | Dowell et al. | 424/70.1 |
| 5,393,450 A | * | 2/1995 | Shana'a | 252/170 |
| 5,393,519 A | * | 2/1995 | Dowell et al. | 424/70.11 |
| 5,403,517 A | * | 4/1995 | Horinishi et al. | 252/551 |
| 5,415,857 A | | 5/1995 | Robbins et al. | |
| 5,534,265 A | | 7/1996 | Fowler et al. | |
| 5,641,480 A | * | 6/1997 | Vermeer | 424/70.24 |
| 5,683,685 A | * | 11/1997 | Hirano et al. | 424/78.03 |
| 5,741,855 A | | 4/1998 | Kaduk et al. | |
| 5,747,435 A | | 5/1998 | Patel | |
| 5,756,439 A | * | 5/1998 | He et al. | 510/159 |
| 6,165,454 A | | 12/2000 | Patel et al. | |

FOREIGN PATENT DOCUMENTS

| | | |
|---|---|---|
| DE | 197 52 067 A1 | 12/1996 |
| GB | 1166062 | 10/1969 |
| WO | WO 99/13830 | 9/1997 |
| WO | WO 98/44896 | 11/1997 |

* cited by examiner

*Primary Examiner*—Charles Boyer
(74) *Attorney, Agent, or Firm*—Rosemary M. Miano

(57) ABSTRACT

A pearlized cleansing composition for personal care comprising:

(a) 4.00–30.00 weight % of an anionic material selected from the group consisting of water soluble lipophilic sulfates and sulfonates of 8 to 22 carbon atoms;

(b) 0.25–4.0 weight % behenyl alcohol; and (c) water.

25 Claims, No Drawings

SHAMPOOS WITH BEHENYL-ALCOHOL

FIELD OF THE INVENTION

This invention relates to the cleansers such as shampoos, liquid soaps, shower gels and similar products that are able to achieve improved pearlescence as compared to previous products made with other agents. In one aspect of the invention, 2-in-1 products with conditioning agents such as silicones are made which not only have improved pearlescence, but also have good stability.

BACKGROUND OF THE INVENTION

A variety of cleansers, especially conditioning cleansers such as shampoos (so called "2-in-1" products), liquid soaps and shower gels are available. Such products use silicones of various types in combination with some type of suspending agent of system. For example, U.S. Pat. No. 4,741,855 to Grote et al uses long chain esters of ethylene glycol, esters of long chain fatty acids, or long chain amine oxides as stabilizing agents. U.S. Pat. No. 6,165,454 to Patel et al, describes the use of selected acrylates such as Aculyn-33 as a suspending agent. U.S. Pat. No. 5,213,716 to Patel et al describes the use of long chain alcohols such as C20–C40 alcohols as stabilizers for silicone containing hair care compositions. Other patents as background include U.S. Pat. No. 5,348,736 to Patel et al; U.S. Pat. No. 5,051,250 to Patel et al; U.S. Pat. No. 5,106,613 to Hartnett et al; and U.S. Pat. No. 4,997,641 to Hartnett et all. Certain commercial products have tried using a combination of cetyl and stearyl alcohols for a stabilizing effect.

These previous attempts have resulted in some degree of success, but there still remains a need to obtain additional pearlizers, especially pearlizers which are capable of stabilizing compositions which contain silicones. In one particular embodiment, formulations are made which not only achieves good pearlescence, but also stabilizes cleansing compositions containing silicones at lower temperatures.

BRIEF SUMMARY OF THE INVENTION

The invention comprises the use of behenyl alcohol, a straight chain alkyl with an average of 22 carbons, in cleansers, especially shampoos. In one particular type of cleansers, a conditioning agent is also present. In particular, compositions of this invention comprise:

(a) 4.00–30.00 weight % (for example, 7–20 weight %) of an anionic material selected from the group consisting of water soluble lipophilic sulfates and/or sulfonates of 8 to 22 carbon atoms, preferably of 10 to 16 or 10 to 18 carbon atoms, more preferably of 10 to 14 or 16 carbon atoms;

(b) 0.25–4.0 weight % (for example, 1–2 weight %) behenyl alcohol.

(c) 0–10.00 weight 5 (particularly 0.10–10.00 weight %) (for example, 0.5–4.0 weight %) of a non-ionic material selected from the group consisting of a higher fatty alkanolamide such as those having 8–22 carbons, for example, cocodiethanolamide, cocoethanolamide, cocoamidopropyl dimethylamine, coco amine, cocoamine oxide, and cocoaminopropionic acid;

(d) 0–10.00 weight % (for example, 0.05–10.00 weight % and more particularly 1–3 weight %) of an amphoteric material (sometimes referred to as a zwitterionic material) selected from the group consisting of derivatives of aliphatic quaternary ammonium, phosphonium or sulfonium compounds in which the aliphatic radicals can be straight chain or branched, and wherein one of the aliphatic substituents contains from 8–22 carbons and one contains an anionic water-solubilizing group (for example, a carboxyl, sulfonate, sulfate, phosphate or phosphonate) C8–C18 alkyl betaines and sulfobetaines, and C8–C18 alkyl amphoacetates and propionates;

(e) optionally a cationic material which is a cationic surface active fiber conditioning agent, which may be considered to be secondary conditioning agents in the invented fiber conditioning compositions, are selected from the group consisting of (i) 0–5.0 weight % (for example, 0.05–5.0 weight % and more particularly 0.2–0.5 weight %) of one or more quaternary ammonium salts of formula:

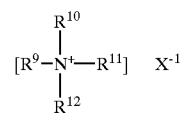

wherein $R^9$ is a lower alkyl having 1–4 carbons; $R^{10}$ and $R^{11}$ may be the same or different and are each selected from the group of higher alkyls having 10–40 carbons; $R^{12}$ is selected from the groups defined for $R^9$ and $R^{10}$; $X^-$ is a salt forming anion selected from the group consisting of a halide (for example, chloride and bromide), lower (C1–C3) alkylsulfates (for example, methosulfate and ethosulfate), lower (C1–C3) carboxylic acid radicals (for example, acetate) and citrate; and (ii) 0.0–2.0 weight % (for example, 0.05–0.4 weight %) of one or more water soluble cationic cellulosic polymers selected from the group consisting of hydroxy alkyl celluloses, alkyl hydroxy alkyl celluloses, galactomannan gums;

(f) 0–5 weight % (for example, 0.25–5.0 weight % and more particularly 0.25–4 weight %) of a silicone selected from the group consisting of water insoluble organosilicone compounds selected from the group consisting of:

(i) dimethicones, dimethicone derivatives and mixtures of the foregoing having a viscosity in the range of 5–100,000 centipoise (cps), particularly 30–70,000 cps and even more particularly 60,000 cps; for example organosilicone compounds of

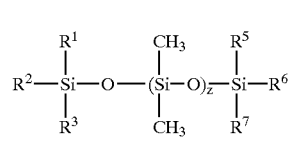

Formula I wherein $R^1$, $R^2$, $R^3$, $R^5$, $R^6$, and $R^7$ may be the same or different and are each independently selected from the group consisting of alkyls of 1–6 carbons (especially 1–2 carbons) and z is selected so that the viscosity described above is achieved; and (ii) aminosilicones of Formula II

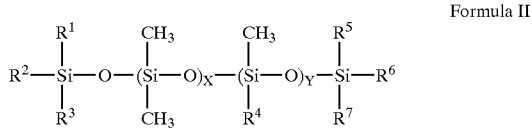

wherein $R^1$, $R^2$, $R^3$, $R^5$, $R^6$, and $R^7$ may be the same or different and are each independently selected from the group consisting of are alkyls of 1–6 carbons (especially 1–2 carbons); and $R^4$ is $R^8$—NH—$CH_2CH_2$—$NH_2$, $R^8$ is an alkylene of 3–6 carbons; x=is an average value and is a number in the range of 500–10,000, particularly 500–4,000, more particularly 500–1000, and especially 750–800; and y=is an average value and is a number in the range of 1–10, particularly less than 5 and especially 1.

(iii) mixtures of (i) and (ii), especially mixtures where high viscosity materials are mixed with lower viscosity materials (examples of suitable materials include a dimethicone from Dow Corning (Midland, Mich.) known as Dow Coming Fluid 200, and a dimethicone from Union Carbide (Tarrytown, N.Y. known as Silicone L-45);

(g) optionally, one or more members selected from the group consisting of an effective amount of a pH modifying agent; an effective amount of a viscosity modifying agent; an effective amount of a preservative; fragrance, a coloring agent; and (h) the remainder water; provided that if silicone is used, a sufficient amount of behenyl alcohol or behenyl alcohol in combination with an additional suspending agent is used to stabilize the composition.

Note, that although other surface active compounds with fiber conditioning properties may also be employed, at least in part. Thus, imidazolinium salts and betaines, and such cationic and amphoteric materials as are described in U.S. Pat. No. 4,000,077 may be substituted for at least some of the quaternary ammonium salt, as may be complexes of cationic and anionic surfactants such as have been described in U.S. Pat. Nos. 4,786,422; 4,888,119; and 4,929,367, which are incorporated by reference herein as to the description of these materials.

DETAILED DESCRIPTION OF THE INVENTION

For the anionic materials (also referred to herein as anionic surfactants or anionic detergents), examples include higher (C8–18) alkyl sulfates, higher paraffin sulfonates, higher olefin sulfonates, higher fatty acid monoglyceride sulfates, higher fatty alcohol lower alkoxy (and polyoxy) sulfates, linear higher alkyl benzene sulfonates, and dialkyl sulfosuccinates. The most preferred of these anionic detergents for the examples of shampoos described herein are the higher alkyl sulfates of 10 to 16 carbon atoms and the higher alkyl lower alkoxy sulfates of 10 to 18 carbon atoms (preferably with the higher alkyl thereof being lauryl and with 2 or 3 ethoxy groups per mole). However, such alkyls may be of 10 to 16 carbon atoms and the alkoxy content may be of 1 to 20 per mole, such as 2 to 6 ethoxy groups per mole. A most preferred higher fatty alcohol sulfate is lauryl sulfate and a particularly preferred higher fatty alcohol poly-lower alkoxy sulfate is di- or triethoxylated lauryl alcohol sulfate. Most preferably the anionic detergent will be a mixture of higher alkyl sulfate and higher alkyl ether sulfate, with either being present in greater or equal proportion, and with the ratio of amounts of such components being in the range of 10:1 to 1:10 or 7:1 to 1:7, for example, 1:5 to 5:1, when both such anionic detergents are present.

The anionic detergents will be employed in the forms of their water soluble salts, which will usually be salts of alkali metals (sodium, potassium), ammonium, amines (such as dimethylamine and trimethylamine) or lower alkanolamines (such as triethanolamine, diethanolamine and monoethanolamine). Exemplary of useful detergents are ammonium lauryl sulfate, sodium lauryl diethoxy sulfate, arumonium lauryl triethoxy sulfate, sodium alpha C16 olefin sulfonate, sodium C14 paraffin sulfonate, sodium coco monoglyceride sulfate, triethanolamine cetyl sulfate and dimethylamine myristyl sulfate. However, for best results it is preferred to utilize higher alkyl sulfate, higher alkyl poly-lower alkoxy sulfate or a mixture of such higher alkyl sulfate and such higher alkyl ether sulfate, such as lauryl sulfate and lauryl diethoxy sulfate or lauryl triethoxy sulfate, often with the higher alkyl sulfate being present in greater proportion and in ammonium, triethanolamine and/or sodium salt form. (See U.S. Pat. No. 5,415,857 assigned to Colgate-Palmolive Co.)

One particular group of anionic materials useful in this invention include 4–30 weight % (especially 5–20 weight %) of one or a mixture of ammonium lauryl sulfate and sodium laureth (with 2 moles ethylene oxide) sulfate.

Non-ionic materials useful in this invention include higher fatty alkanolamides which have long been known as foaming agents and foam stabilizers. Such compounds will usually have 8–22 carbon atoms in the compounds and have, for example, 12 to 16 carbon atoms in the acyl group, which is reacted with a lower (1 to 3 carbon atoms) mono- or dialkanolamine. In the present formulations the best alkanolamides are considered to be lauric monoethanolamide, cocodiethanolamnide and cocoethanolamide.

Amphoteric materials (also referred to herein as amphoteric surfactants or zwitterionic materials) can be exemplified by those which can be broadly described as derivatives of aliphatic quaternary ammonium, phosphonium, or sulfonium compounds in which the aliphatic radicals can be straight chain or branched, and wherein one of the aliphatic substituents contains from about 8–18 carbons and one contains an anionic water-solubilizing group such as a carboxyl, sulfonate, sulfate, phosphate or phosphonate group. These can generally be represented by the following formula

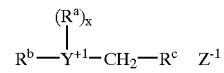

wherein $R^a$ is a C1–3 alkyl or monohydroxy alkyl; $R^b$ is a C8–18 alkyl, alkenyl or hydroxy alkyl radical with 0–10 ethylene oxide moieties and 0–1 glyceryl moiety; $R^c$ is a C1–4 alkylene or hydroxyalkylene, x is 1 when Y is a sulfur atom and X is 2 when Y is a nitrogen or phosphorous atom, Z is a radical selected from the group consisting of carboxylate, sulfonate, sulfate, phosphonate, and phosphate groups.

One group of amphoteric includes
  4-[N,N-di(2-hydroxyethyl)-N-octadecylammonio]-butane-1-carboxylate;
  5-[S-3-hydroxypropyl-S-hexadecylsulfonio]-3-hydroxypentae-1-sulfate;
  3-[P,P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphonate;

3-[N,N-dimethyl-N-hexadecylammonio]-propane-1-sulfonate;

4-[N,N-di(2-hydroxyethyl)-N-(2-hydroxydodecyl) arnmonio]-butane-1-carbonate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-32-hydroxypentane-1-sulfate.

Another group of amphoteric materials are the betaines such as high alkyl betaines including cocodimethyl carboxymethyl betaine, lauryl dimethyl carboxymethyl betaine, lauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl)-carboxymethyl betaine, oleyl dimethyl gamma-carboxypropyl betaine, lauryl bis-(2-hydroxypropyl)alpha-carboxyethyl betaine, etc. (See U.S. Pat. No. 4,741,855 assigned to the Procter & Gamble Co.)

Particular examples of amphoteric materials include cocoamidopropyl betaine, cocobetaine, cocosultaine, especially when one or more of non-ionic and zwitterionic materials can be used, and where the total of non-ionic and zwitterionic material are in the range of 5–10 weight %.

Generally amphoteric surfactants will be selected from the group consisting of C8–18 alkyl betaines and sulfobetaines, and C8–18 alkyl amphoacetates and propionates. Suitable betaines and sulfobetaines have the formula

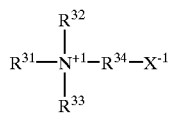

where $R^{31}$=C8–C22 alkyl, $R^{35}$ CO— (where $R^{35}$=C8–C22), $R^{36}$—C(O)—NH$_2$—(CH$_2$)$_3$— (where $R^{36}$=C8–C22);

$R^{32}$=C1–C4 alkyl;

$R^{33}$=C1–C4 alkyl;

$R^{34}$=C1–C4 alkyl;

and $X^{-1}$=is selected from the group consisting of COO$^{-1}$; OSO$_3^{-1}$; CH$_3$CH$_2$COO$^{-1}$ Other amphoteric materials include compounds of formula

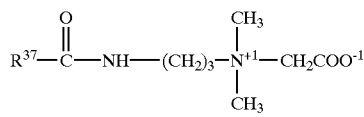

where $R^{37}$=cocoyl.

Typical betaines and amido alkyl betaines include decyl dimethyl betaine or 2-(N-decyl-N,N-dimethylammonio) acetate, cocodimethyl betaine or 2-(N-coco-N,N-dimethylammonio) acetate, myristyl dimethyl betaine, palmityl dimethyl betaine, lauryl dimethyl betaine, cetyl dimethyl betaine, stearyl dimethyl betaine, cocoamidopropyl dimethyl betaine and laurylmidoethyl dimethyl betaine. Typical sulfobetaines or sultaines similarly include cocodimethyl sulfobetaine, or 3-(N-coco-N,N-dimethylammonio) propane-1 sulfonate, myristyl dimethyl sulfobetaine, lauryl dimethyl sulfobetaine, cocoamidoethyl-sulfobetaine and cocamidopropylhydroxy sultaine.

Another group of suitable amphoteric surfactants are the C8–C18 alkyl amphoacetates and propionates corresponding to the following formula:

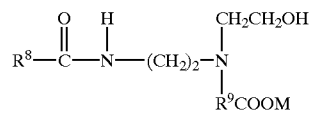

wherein $R^8$ C(O) is a C8–C18 acyl group, $R^9$ is a methyl or ethyl group, and M is a salt forming group such as sodium or potassium. A substitute for the described amphoacetate or amphopropionate compound is sodium cocoamphohydroxypropyl sulfonate. Sodium cocoamphoacetate is a preferred material. (See U.S. Pat. No. 5,747,435).

When an amphoteric surfactant is used in the compositions of the invention (especially shampoos), the proportion of the amphoteric surfactant generally will be in the range of about 2.5% to about 21% by weight of the final composition. A particular proportion of amphoteric surfactant will be selected from the range of about 4% to about 13% by weight and, more particularly, from the range of about 6% to about 10% by weight of the final composition.

In a particular group of compositions, the proportion of the surfactant mixture (total of all surfactants used) will be from about 8% to 28% by weight of the composition; and in a more particular composition the proportion of the surfactant mixture will be from 13% to 22% by weight.

For the cationic material the preferred quaternary ammonium salts are of the formula

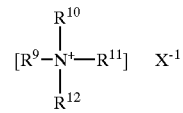

[$R^9 R^{10}$ $R^{11}$ $R^{12}$ N+][$X^{-1}$], wherein at least one of the R groups is lower alkyl and at least one is higher alkyl, with the others being higher and/or lower alkyl. Preferably $R^9$ is lower alkyl, such as of 1 to 4 carbon atoms, $R^{10}$ and $R^{11}$ are higher alkyls of 10 to 40 carbon atoms, $R^{12}$ is such a higher alkyl or lower alkyl, and X$^-$ is a salt forming anion selected from the group consisting of halides (for example, chloride and bromide), lower (C1–C3 alkylsulfate (for example, methosulfate and ethosulfate), lower (C1–C3) carboxylic acid radicals (for example, acetate) and citrate. The lower alkyl will preferably be of 1 to 3 carbon atoms, more preferably being of 1 or 2 carbon atoms, and most preferably, in most cases, will be methyl, and the higher alkyl will preferably be of 10 to 22 carbon atoms, more preferably 12 to 18 or 20 carbon atoms, most preferably of 14 to 18 carbon atoms, for example, 16 or about 16 carbon atoms. The anion is preferably a alogen, such as chlorine, bromine or iodine, with chlorine and bromine being preferred and with chlorine being more preferred. The number of lower alkyls on the quaternary nitrogen will preferably be 1 or 2 and the number of higher alkyls will usually be 2 or 3. It has been found to be desirable to have at least 30 carbon atoms in the quaternary ammonium salt and preferably at least 34. The most preferred higher alkyl is cetyl, the most preferred lower alkyl is methyl, and the most preferred quaternary ammonium halide is tricetyl methyl ammonium chloride. Nevertheless, it is within the invention to employ other quaternary ammonium halides, such as distearyl dimethyl ammonium chloride, dilauryl dimethyl ammonium bromide, stearyl cetyl dimethyl ammonium chloride, trimyristyl ethyl ammonium bromide and trilauryl ethyl ammonium chloride, and other fiber and hair conditioning cationic surfactants as at least part of the fiber and/or hair conditioning cationic surfactant (surfactant is short for surface active agent) content of the present compositions.

Another category of cationic materials are natural polymers such as hydroxy alkyl celluloses and alkyl hydroxy alkyl celluloses. Cationic hydroxy alkyl celluloses and their preparation are described in British Patent Number, 1,166, 062 assigned to Union Carbide and U.S. Pat. No. 5,747,435 assigned to Colgate-Palmolive Co. These hydroxy ethyl celluloses are marketed under the trade designation JR 125, JR 30M, and JR 400 and are believed to have a molecular weight in the range of 150,000–400,000 and a degree of substitution of a quaternary group of about 0.3. Alkyl hydroxy alkyl celluloses having the same formula as hydroxy alkyl cellulose, but with additional alkyl substituents at other sites on the anhydroglucose unit are also available. More particularly, the ethyl hydroxy ethyl celluloses are available under the tradename "Modocoll" with a molecular within the range of about 50,000–500,000 and a degree of substitution of about 0.1–0.8. Other suitable natural cationic polymers are the galactomannan gums, for example, guar gum and hydroxy alkylated guar gum. The molecular weight of guar gum is believed to be in the range of 100,000–1,000,000. A suitable cationic guar gum carrying the group —CH$_2$CH=CHCH$_2$N(CH$_3$)C— with a degree of substitution of about 0.2–0.8 is commercially available under the tradenames Jaguar C-17 and C-13. The preferred cationic cellulose polymer is Polyquaternium-10 which is a polymeric quaternary ammonium salt of hydroxyethyl cellulose reacted with a trimethyl ammonium substituted epoxide. The proportion of the cationic natural polymer may be, for example, in he range of about 0.05–1.0%, particularly 0.1–0.8% and, more particularly, in the range of about 0.2–0.7% by weight of the final composition. When the cationic natural cellulose or galactomannan gum polymers are used, up to one-half of their weight many be substituted by a second non-cellulosic, cationic polymer that is soluble in the final composition. Examples of these include dialkyldiallyl ammonium salt (such as a halide) homopolymers or copolymers, for example, dimethyl ammonium chloride homopolymer, dimethyldiallyl ammonium chloride/acrylamide copolymer containing at least 60% dimethyldiallyl ammonium chloride monomer, dimethyldiallyl ammonium chloride/acrylic acid copolymer containing at least 90% dimethyldiallyl ammonium chloride monomer, vinyl imadazolevinyl pyrrolidone copolymers containing at least 50% vinyl imidazole and polyethyleneimine. Particular examples of cationic polymers include Merquat 100 (a polymer of diallyldimethyl ammonium chloride (charge density of 126)) and Luviquat 905 (a 95% vinyl imidazole/5% vinylpyrrolidone copolymer (charge density of 116)). Other examples include any of the "Polyquaternium-X" compounds where X is a whole number.

Particular cationic materials useful in this invention include one or more member selected from the group consisting of Polyquatemium-6, Polyquaternium-7, Polyquatemium-10, Polyquatemium-16, Polyquaternium-80, cationic guar gum, and distearyl dimonium chloride, wherein the total amount of cationic materials used is in the range of 0.05–1 weight %, especially 0.05–0.5 weight %.

The cationic materials described for this invention are preferably in aqueous form and may be dissolved or dispersed in an aqueous medium such as water.

Silicones useful in this invention include dimetlucones, aminosilicones and dimethiconols, especially dimethicones having a viscosity in the range of 30,000–100,000 centistokes ("cst"), and particularly 60,000 cst. Example of such materials include the silicones listed in Tables A, C, E, G, I, K, M, O, Q, S, U, W, Y, AA, AC, AF, and AM.

One particular class of silicones is dispersed, insoluble, non-volatile silicone (especially polydimethylsiloxane). In one embodiment, 4–30 weight % of the anionic marterial; 0.1–10 weight % of a dispersed, insoluble, non-volatile silicone (especially polydimethylsiloxane) and sufficient behenyl alcohol to stabilize the silicone are used.

The target pH of the compositions of the invention is in the range of 5.5–6.8, especially in the range 6.0–6.5. Agents suitable for modifying pH include those known in the art, for example, sodium phosphate monobasic and citric acid to decrease pH, and sodium phosphate dibasic and sodium hydroxide to increase pH.

The target viscosity of the compositions of the invention is in the range of 2,000–8,000 centipoise ("cps"). Viscosity modifiers known to those in the are may be used, particularly in the range of 0.1–2.0 weight % (more particularly 0.5 weight %). For example, viscosity may be increased by the addition of sodium chloride and viscosity may be decreased with the addition of sodium cumene sulfonate.

Preservative may be used in amounts in the range of 0.0–0.5%, particularly 0.0–0.1%. Examples include KATHON (for example, effective amounts up to 0.07%), formaldehyde (for example, 0.1–0.2%), hydentoin (for example, effective amounts up to 0.5%) or mixtures of the foregoing.

To make the invented compositions the various required components are dissolved and/or suspended in an aqueous medium. For shampoos, such medium may include various non-interfering normal shampoo composition constituents known in the art, which have been specifically mentioned herein because they are especially desirable components of the present compositions and contribute in a significant manner to its desirable properties.

Behenyl alcohol is used in this invention. This long chain alcohol is preferably a saturated compound, with the hydroxy group being terminally located. Behenyl alcohol will normally be of a distribution of C20–C24 homologous alcohols and typically all are of even numbers of carbon atoms, averaging 22 carbon atoms (on a weight basis). Behenyl alcohol has been found to be especially effective in this invention. (When the average number of carbon atoms in the chain is less than 18 the desired effectiveness of such alcohols in the present formulations is decreased, with the stabilization, fiber conditioning and pearlizing actions being diminished.). In addition to the mentioned long chain alcohols, related compounds such as corresponding alkoxylated alcohols, corresponding fatty acids and long chain saturated primary alcohol esters, may be substituted in a minor proportion (for example, less than 50% of the behenyl alcohol component). When such a substitution is made, ethoxylated alcohols are preferred as the alkoxylated alcohols and will normally contain up to 20 ethoxy groups per mole, such as 10 to 20, for example, about 13 or 15. Thus, the behenyl alcohol normally will be employed alone or in mixture with related compounds from the "derivatives" group, with the alcohol being the major proportion of the final "alcohol plus derivatives" content. Examples of commercial materials which may be employed in the present compositions.

Behenyl C-22 alcohols (having an average of 22 carbon atoms in its chain as described above) may also be used in combination with other ingredients in sufficient amounts to stabilize the final product. Examples of such combinations include, for example, 0.25–4.0 weight % behenyl alcohol plus 0.1–2.0 weight % of an acrylic stabilizing agent selected from the group consisting of polyacrylic acid, derivatives of polyacrylic acid, acrylates copolymer and derivatives of acrylates copolymer such as those sold by Rohm & Haas (Philadelphia, Pa.) under the names Aculyn-22, -28 and -33.

The composition of this invention may be made by a variety of techniques. Such techniques are described in the Examples.

It should be noted that different levels of conditioning may be appropriate for different types of hair. Some types of hair such as bleached or processed hair require high level of conditioning. Other types of hair only need a small amount of conditioning. The compositions of this invention may be formulated to accommodate all types of conditioning requirements.

It should also be noted that while the term "materials" has been used, it is to be understood that for anionic, nonionic and amphoteric components the term "surfactants" or "detergents" could also be used.

EXAMPLES

The following Examples are offered as illustrative of the invention and are not to be construed as limitations thereon. In the Examples and elsewhere in the description of the invention, chemical symbols and terminology have their usual and customary meanings. Temperatures are in degrees Celsius unless otherwise indicated. The amounts of the components in the Examples as well as elsewhere in the application, are in weight percents based on the standard described; if no other standard is described then the total weight of the compositions is to be inferred. Various names of chemical components used in this application include those listed in the *CTFA International Cosmetic Ingredient Dictionary* (Cosmetics, Toiletry and Fragrance Association, Inc., 4$^{th}$ ed. 1991).

General Example A

Method of Making Conditioning Shampoo

The main mixing vessel should be stainless steel (for example, 304L/316L), equipped with a variable speed mixer such as a Lightnin' Mixer. A separate stainless steel vessel (for example, 304L/316L), equipped with facilities for heating and minimal mixing, is required for the cocodiethanolamide ("CDEA") premix. Other separate stainless steel or plastic vessels are required for other premixes. Other utensils may be needed. Vacuum equipment is not required; but care must be taken not to promote foam formation.

To the main mixing vessel, add deionized water. Begin mixing and heating. In the following order, add tetrasodium EDTA, sodium phosphate dibasic, and an anionic surfactant (for example, ammonium lauryl sulfate ("ALS") and/or sodium laureth-2-sulfate ("SLES")). Allow sufficient time for each material to fully dissolve. Mix the batch for at least 15 minutes, or until clear and uniform. Heat to 75–80° C. This is the water phase, or phase I.

To a separate, heatable, dry, clean container, add cocodiethanolamide ("CDEA"), behenyl alcohol, a cationic material (such as distearyl dimmonium chloride ("DSDAC") (if any is used)), and a cationic material such as guar gum (if any is used). Heat with stirring to 85–90° C. Continue mixing until all solids are completely dissolved and the solution is uniform. This is phase II. When phase II is at the proper temperature (85–90 degrees C.), this phase is added to the main mixing vessel to phase. The combined phases are then mixed until uniform (about 20 minutes) and then heating is stopped.

To a separate, dry, clean container, add deionized water. Add Polyquaternium-6 (if any is used), Polyquaternium-7 (if any is used), Polyquaternium-10 (if any is used), or Polyquatemium-16 (if any is used). Mix the ingredients well until the mixture is clear and uniform. Add this separate mixture to the main mixing vessel. Mix the combined ingredients until uniform (at least an additional 15 minutes).

Begin cooling the batch. To the main mixing vessel, add acrylates copolymer (if any is used). Mix the batch until uniform (at least an additional 15 minutes).

To the main mixing vessel, add dimethicone. Mix batch until uniform (at least 20 minutes).

To the main mixing vessel, add betaine (if any is used). Mix the batch until uniform (at least an additional 15 minutes).

To the main mixing vessel, add perfume (if any is used). Mix the batch until uniform (at least an additional 15 minutes).

To the main mixing vessel, add color(s) (if any are used). Mix the batch until uniform (at least an additional 15 minutes).

To the main mixing vessel, add preservative(s) (if any are used). Mix the batch until uniform (at least an additional 15 minutes).

Specifications are checked on a batch sample which is centrifuged to remove air and cooled to 25° C. If necessary, add sodium cumene sulfonate ("SCS") to the batch to reduce viscosity. It is preferred that no more than 2% total additional materials be added, or the stability of the final product may be reduced. Mix the batch for at least 15 minutes, or until uniform. Recheck batch specifications; if all is acceptable, discharge the batch through a 20 mesh or equivalent filter when the temperature has cooled below 30° C. Target specifications are listed in the following chart:

| Specification | Requirement* | Measurement notes |
|---|---|---|
| Product appearance | To match control | To match control |
| Viscosity | 3750–4250 cps | Brookfield RVTD Viscometer, Spindle #4, 20 rpm, @ 25° C., 60 seconds |
| pH | 6.0–6.5 | as is @ 25° C. |
| Specific Gravity | 1.010 ± 0.01 | @ 25° C. |

General Example B

Protocol for Evaluating Stability of Shampoo

In order to evaluate the stability of shampoo samples (including, physical stability under various accelerated aging conditions and fragrance stability for selected samples), a sample size of 250 ml was placed in a series of 300 ml glass jars to test stability at various accelerated aging conditions. One sample was placed in a glass jar for initial preservation effectiveness test (described below); one sample was placed in a plastic bottle (original packaging bottle made of polyvinyl chloride) and stored at 43 degrees C. (also for the preservation test described below); one sample was placed in each of 7 jars and aged at −18 degrees C., 4 degrees C., 25 degrees C. (Control), 38 degrees C., 43 degrees C., 49 degrees C., and sunlight; and an additional 3 samples were placed in each of 3 jars for additional testing on fragrance stability at selected temperatures. Samples were evaluated at 4, 8 and 13 weeks.

For stability testing, the samples aged at −18 degrees C., 4 degrees C., 25 degrees C. (Control), 38 degrees C., 43 degrees C., 49 degrees C., and sunlight were tested at 4, 8 and 13 weeks. For each test the samples were first equilibrated to 25 degrees C. and visually inspected. The physical appearance of the samples was compared to the Control and to the other samples. Any observable changes (including separation of layers, changes in consistency (thermodynamic stability), and differences in color, clarity and pearlescence) were noted. Brookfield viscosity measurements were taken using the conditions described above as well as pH measurements and the values were compared to initial sample tested right after manufacture. The samples were then returned to their respective aging conditions until the next testing time was completed.

For fragrance evaluation, samples were tested by visual inspection according to the following schedule:
 a. 4 weeks at 25° C. and 49° C.
 b. 8 weeks at 25° C. and 43° C.
 c. 13 weeks at 25° C. and 43° C.

Any separation, changes in color, etc. were noted. After each testing period the samples are returned to their specified conditions.

For preservation effectiveness testing an antimicrobial preservation efficacy test can be used. Test products are innoculated with two mixed batteries of microorganisms of known quantities (one bacterial, one fingal) and monitored for survival at 7 days. The samples are then re-inoculated and further monitored at designated test points. The media that can be used includes Eugon broth (used for bacterial and yeast cultures), Czapek solution agar and Mycological agar (used for mold cultures). The media is prepared, dispensed into suitable tubes and sterilized. (Slanted tubes may be used as desired.) Modified letheen agar ("MLA") and TAT broth are also used, but the MLA must be held at 46 degrees C. in a waterbath until used. Sterile saline (0.85% adjusted to a pH of 6–7 with 1N NaOH or 1N HCl) with 9 ml amounts in test tubes is used for innoculum counts. Any materials held over 7 days must have additional storage accommodations such as refrigeration. Suitable techniques should be used depending on the viscosity of the samples to be tested. Materials should be screened for contaminations before testing. Cultures of microorganisms may be obtained from Chrisope Technologies (Lake Charles, La.) or American Type Culture Collection (Manassas, Va.). Product spoilage isolates will also be included in the innoculum pool. Suitable innoculation techniques, incubation times/temperatures, and evaluation of samples known to those skilled in the art may be used.

For pearlescence evaluation the following "low" and "high" control samples were prepared with ethylene glycol distearate ("EGDS") as the pearlizer. Visual observations were done and the amount of pearlizing effect was rated.

| Sample 1-low | Sample 2-medium | Sample 3-high |
| --- | --- | --- |
| 0.75% EGDS | 1.50% EGDS | 2.25% EGDS |
| Poor pearlizing | Good pearlizing | Very good pearlizing |

A sample of each of the high and low controls as well as a sample of the formulation made according to the invention was placed in each of three 200 ml glass jars. The samples were allowed to sit undisturbed overnight. The three jars were then shaken by hand at least ten times each to generate a pearlescence pattern. Using a scale of light, acceptable, high and very high, the samples were observed visually and assigned a rank.

General Example C

Evaluation of Conditioning Ability Using Tress Test

The ability of shampoo compositions to condition hair can be evaluated using the following method. Sample of tresses (about 3.2 grams per tress) were obtained. Samples included Asian and European hair that was about 20–30 cm (8–12 inches) long. The tresses were pretreated by thoroughly wetting all tresses with water that is at a temperature of 40.56 degrees C. (105° F.). Using a hypodermic syringe or squirt/wash bottle, approximately 3 ml of a freshly prepared 15% aqueous solution of sodium laureth (2EO) sulfate is placed on the tress. This solution is worked through the hair with an up and down motion for 30 seconds, evenly coating the hair. Care should be taken so that the top (root) end, as well as the tip end are both reached. The tress is then rinsed for 30 seconds. The last two steps are repeated for all tresses, rinsing for as long as necessary to remove all lather. For the treatment procedure, the tresses are coded with non-water soluble marker or tape so that the tester cannot tell which sample has what composition; a minimum of 2 tresses is required for each product tested, if statistical results are expected. Using a hypodermic syringe, 1 ml of the test shampoo is placed on the selected tress. The tress is worked between the fingers in an up and down motion for one minute, evenly coating the hair. Care should be taken to reach to top (root) end, as well as the tip end. The tress is then rinsed thoroughly for 30 seconds under 40.56 degrees C. (105° C.) tap water. The last two steps are repeated for each tress using a separate sample for each tress. All the tresses are then rinsed thoroughly for 60 seconds under 40.56 degrees C. (105° C.) tap water. (Temperatures were checked with installed thermometers.)

For the evaluation process itself, a wet combing test is used if used first followed by a dry combing test. For the wet combing test, a separate comb is used for each tress and coded to match the particular tress. The tresses are hung above a sink, trough or paper towels. The tresses are arranged in random order and kept wet (lightly dripping) with deionized water using a wash or trigger type squirt bottle. Trained evaluators are used one at a time to comb the tresses and assign a rank order using a scale from 1 to 10 with 1 being the hardest to comb and 10 being the easiest to comb. Using the fine teeth of the comb, judges comb the tresses, move them, and place them in descending order from easiest-to-hardest to comb. The tresses are then called Ranked and the order recorded (preferably without duplication of rank). The judge then assigns a rating of 1 to 10 to each tress using his/her own subjective basis. Duplicate ratings are allowed on this scale. After the first judge has completed the process, the tresses are re-randomized and the process repeated. A minimum of 10 judges' evaluations are required if statistical results are expected. For dry combing evaluation, the process described for wet combing is repeated but with dry tresses (preferably air dried). A computer program can be used to evaluate data.

Examples 1–5

General Method A may be used to make the compositions listed in Table A with the amounts of ingredients indicated.

The compositions of Examples 1–5 were evaluated for stability, pearlescence, and conditioning ability using the procedures listed above under General Examples B and C. The results are in Table B.

TABLE A

| Ingredient | Ex. 1 | Ex. 2 | Ex. 3 | Ex. 4 | Ex. 5 |
|---|---|---|---|---|---|
| Ammonium lauryl sulfate | 5.00 | 8.00 | 10.00 | 14.00 | 18.00 |
| Sodium laureth (2EO) sulfate | — | — | — | — | — |
| Cocoamidopropyl betaine | 2.00 | 2.00 | 2.00 | 2.00 | 2.00 |
| Cocodiethanolamide | — | — | — | — | — |
| Polyquaternium-6 | 0.20 | 0.20 | 0.20 | 0.20 | 0.20 |
| Polyquaternium-7 | — | — | — | — | — |
| Polyquaternium-10 | — | — | — | — | — |
| Polyquaternium-16 | — | — | — | — | — |
| Cationic guar gum | — | — | — | — | — |
| Distearyl dimonium chloride | — | — | — | — | — |
| Fragrance | ±1.50 | ±1.50 | ±1.50 | ±1.50 | ±1.50 |
| Color | ±0.10 | ±0.10 | ±0.10 | ±0.10 | ±0.10 |
| Preservative | ±1.00 | ±1.00 | ±1.00 | ±1.00 | ±1.00 |
| Behenyl alcohol | 1.00 | 1.00 | 1.00 | 1.50 | 2.00 |
| Dimethicone (60,000 cst) | 0.25 | 0.50 | 1.00 | 2.00 | 2.00 |
| pH modifier | ±1.00 | ±1.00 | ±1.00 | ±1.00 | ±1.00 |
| Viscosity modifier | ±1.00 | ±1.00 | ±1.00 | ±1.00 | ±1.00 |
| Water | 86.95 | 83.70 | 81.20 | 75.70 | 71.20 |

TABLE B

| Property | Ex. 1 | Ex. 2 | Ex. 3 | Ex. 4 | Ex. 5 |
|---|---|---|---|---|---|
| Stability | Yes | Yes | Yes | Yes | Yes |
| Pearlescence | Acceptable | Acceptable | Acceptable | Acceptable | High |
| Conditioning | 5.00 | 6.00 | 7.00 | 8.00 | 8.50 |

These compositions show stability and pearlesence.

Examples 6–10

General Method A may be used to make the compositions listed in Table C with the amounts of ingredients indicated. The compositions of Examples 6–10 may be evaluated for stability, pearlescence, and conditioning ability using the procedures listed above under General Examples B and C. The results are in Table D.

TABLE C

| Ingredient | Ex. 6 | Ex. 7 | Ex. 8 | Ex. 9 | Ex. 10 |
|---|---|---|---|---|---|
| Ammonium lauryl sulfate | 5.00 | 8.00 | 10.00 | 14.00 | 18.00 |
| Sodium laureth (2EO) sulfate | — | — | — | — | — |
| Cocoamidopropyl betaine | 2.00 | 2.00 | 2.00 | 2.00 | 2.00 |
| Cocodiethanolamide | — | — | — | — | — |
| Polyquaternium-6 | — | — | — | — | — |
| Polyquaternium-7 | 0.20 | 0.20 | 0.20 | 0.20 | 0.20 |
| Polyquaternium-10 | — | — | — | — | — |
| Polyquaternium-16 | — | — | — | — | — |
| Cationic guar gum | — | — | — | — | — |
| Distearyl dimonium chloride | — | — | — | — | — |
| Fragrance | ±1.50 | ±1.50 | ±1.50 | ±1.50 | ±1.50 |
| Color | ±0.10 | ±0.10 | ±0.10 | ±0.10 | ±0.10 |
| Preservative | ±1.00 | ±1.00 | ±1.00 | ±1.00 | ±1.00 |
| Behenyl alcohol | 1.00 | 1.00 | 1.00 | 1.50 | 2.00 |
| Dimethicone (60,000 cst) | 0.25 | 0.50 | 1.00 | 2.00 | 2.00 |
| pH modifier | ±1.00 | ±1.00 | ±1.00 | ±1.00 | ±1.00 |
| Viscosity modifier | ±1.00 | ±1.00 | ±1.00 | ±1.00 | ±1.00 |
| Water | 86.95 | 83.70 | 81.20 | 75.70 | 71.20 |

TABLE D

| Property | Ex. 6 | Ex. 7 | Ex. 8 | Ex. 9 | Ex. 10 |
|---|---|---|---|---|---|
| Stability | Yes | Yes | Yes | Yes | Yes |
| Pearlescence | Acceptable | Acceptable | Acceptable | Acceptable | High |
| Conditioning | 5 | 6 | 7 | 8 | 8.5 |

These compositions show stability and pearlesence.

Examples 11–15

General Method A may be used to make the compositions listed in Table E with the amounts of ingredients indicated. The compositions of Examples 11–15 may be evaluated for stability, pearlescence, and conditioning ability using the procedures listed above under General Examples B and C. The results are in Table F.

TABLE E

| Ingredient | Ex. 11 | Ex. 12 | Ex. 13 | Ex. 14 | Ex. 15 |
|---|---|---|---|---|---|
| Ammonium lauryl sulfate | 5.00 | 8.00 | 10.00 | 14.00 | 18.00 |
| Sodium laureth (2EO) sulfate | — | — | — | — | — |
| Cocoamidopropyl betaine | 2.00 | 2.00 | 2.00 | 2.00 | 2.00 |
| Cocodiethanolamide | — | — | — | — | — |
| Polyquaternium-6 | — | — | — | — | — |
| Polyquaternium-7 | — | — | — | — | — |
| Polyquaternium-10 | 0.20 | 0.20 | 0.20 | 0.20 | 0.20 |
| Polyquaternium-16 | — | — | — | — | — |
| Cationic guar gum | — | — | — | — | — |
| Distearyl dimonium chloride | — | — | — | — | — |
| Fragrance | ±1.50 | ±1.50 | ±1.50 | ±1.50 | ±1.50 |
| Color | ±0.10 | ±0.10 | ±0.10 | ±0.10 | ±0.10 |
| Preservative | ±1.00 | ±1.00 | ±1.00 | ±1.00 | ±1.00 |
| Behenyl alcohol | 1.00 | 1.00 | 1.00 | 1.50 | 2.00 |
| Dimethicone (60,000 cst) | 0.25 | 0.50 | 1.00 | 2.00 | 2.00 |
| pH modifier | ±1.00 | ±1.00 | ±1.00 | ±1.00 | ±1.00 |
| Viscosity modifier | ±1.00 | ±1.00 | ±1.00 | ±1.00 | ±1.00 |
| Water | 86.95 | 83.95 | 81.95 | 77.95 | 73.95 |

TABLE F

| Property | Ex. 11 | Ex. 12 | Ex. 13 | Ex. 14 | Ex. 15 |
|---|---|---|---|---|---|
| Stability | Yes | Yes | Yes | Yes | Yes |
| Pearlescence | Acceptable | Acceptable | Acceptable | Acceptable | High |
| Conditioning | 5 | 6 | 7 | 8 | 8.5 |

These compositions show stability and pearlesence.

Examples 16–20

General Method A may be used to make the compositions listed in Table G with the amounts of ingredients indicated. The compositions of Examples 16–20 may be evaluated for stability, pearlescence, and conditioning ability using the procedures listed above under General Examples B and C. The results are in Table H.

TABLE G

| Ingredient | Ex. 16 | Ex. 17 | Ex. 18 | Ex. 19 | Ex. 20 |
|---|---|---|---|---|---|
| Ammonium lauryl sulfate | 5.00 | 8.00 | 10.00 | 14.00 | 18.00 |
| Sodium laureth (2EO) sulfate | — | — | — | — | — |
| Cocoamidopropyl betaine | 2.00 | 2.00 | 2.00 | 2.00 | 2.00 |

TABLE G-continued

| Ingredient | Ex. 16 | Ex. 17 | Ex. 18 | Ex. 19 | Ex. 20 |
|---|---|---|---|---|---|
| Cocodiethanolamide | — | — | — | — | — |
| Polyquaternium-6 | — | — | — | — | — |
| Polyquaternium-7 | — | — | — | — | — |
| Polyquaternium-10 | — | — | — | — | — |
| Polyquaternium-16 | 0.20 | 0.20 | 0.20 | 0.20 | 0.20 |
| Cationic guar gum | — | — | — | — | — |
| Distearyl dimonium chloride | — | — | — | — | — |
| Fragrance | ±1.50 | ±1.50 | ±1.50 | ±1.50 | ±1.50 |
| Color | ±0.10 | ±0.10 | ±0.10 | ±0.10 | ±0.10 |
| Preservative | ±1.00 | ±1.00 | ±1.00 | ±1.00 | ±1.00 |
| Behenyl alcohol | 1.00 | 1.00 | 1.00 | 1.50 | 2.00 |
| Dimethicone (60,000 cst) | 0.25 | 0.50 | 1.00 | 2.00 | 2.00 |
| pH modifier | ±1.00 | ±1.00 | ±1.00 | ±1.00 | ±1.00 |
| Viscosity modifier | ±1.00 | ±1.00 | ±1.00 | ±1.00 | ±1.00 |
| Water | 86.95 | 83.70 | 81.20 | 75.70 | 71.20 |

TABLE H

| Property | Ex. 16 | Ex. 17 | Ex. 18 | Ex. 19 | Ex. 20 |
|---|---|---|---|---|---|
| Stability | Yes | Yes | Yes | Yes | Yes |
| Pearlescence | Acceptable | Acceptable | Acceptable | Acceptable | High |
| Conditioning | 5 | 6 | 7 | 8 | 8.5 |

These compositions show stability and pearlesence.

Examples 21–25

General Method A may be used to make the compositions listed in Table I with the amounts of ingredients indicated. The compositions of Examples 21–25 may be evaluated for stability, pearlescence, and conditioning ability using the procedures listed above under General Examples B and C. The results are in Table J.

TABLE I

| Ingredient | Ex. 21 | Ex. 22 | Ex. 23 | Ex. 24 | Ex. 25 |
|---|---|---|---|---|---|
| Ammonium lauryl sulfate | 5.00 | 8.00 | 10.00 | 14.00 | 18.00 |
| Sodium laureth (2EO) sulfate | — | — | — | — | — |
| Cocoamidopropyl betaine | 2.00 | 2.00 | 2.00 | 2.00 | 2.00 |
| Cocodiethanolamide | — | — | — | — | — |
| Polyquaternium-6 | — | — | — | — | — |
| Polyquaternium-7 | — | — | — | — | — |
| Polyquaternium-10 | — | — | — | — | — |
| Polyquaternium-16 | — | — | — | — | — |
| Cationic guar gum | 0.20 | 0.20 | 0.20 | 0.20 | 0.20 |
| Distearyl dimonium chloride | — | — | — | — | — |
| Fragrance | ±1.50 | ±1.50 | ±1.50 | ±1.50 | ±1.50 |
| Color | ±0.10 | ±0.10 | ±0.10 | ±0.10 | ±0.10 |
| Preservative | ±1.00 | ±1.00 | ±1.00 | ±1.00 | ±1.00 |
| Behenyl alcohol | 1.00 | 1.00 | 1.00 | 1.50 | 2.00 |
| Dimethicone (60,000 cst) | 0.25 | 0.50 | 1.00 | 2.00 | 2.00 |
| pH modifier | ±1.00 | ±1.00 | ±1.00 | ±1.00 | ±1.00 |
| Viscosity modifier | ±1.00 | ±1.00 | ±1.00 | ±1.00 | ±1.00 |
| Water | 86.95 | 83.70 | 81.20 | 75.70 | 71.20 |

TABLE J

| Property | Ex. 21 | Ex. 22 | Ex. 23 | Ex. 24 | Ex. 25 |
|---|---|---|---|---|---|
| Stability | Yes | Yes | Yes | Yes | Yes |
| Pearlescence | Acceptable | Acceptable | Acceptable | Acceptable | High |
| Conditioning | 5 | 6 | 7 | 8 | 8.5 |

These compositions show stability and pearlesence.

Examples 26–30

General Method A may be used to make the compositions listed in Table K with the amounts of ingredients indicated. The compositions of Examples 26–30 may be evaluated for stability, pearlescence, and conditioning ability using the procedures listed above under General Examples B and C. The results are in Table L.

TABLE K

| Ingredient | Ex. 26 | Ex. 27 | Ex. 28 | Ex. 29 | Ex. 30 |
|---|---|---|---|---|---|
| Ammonium lauryl sulfate | 5.00 | 8.00 | 10.00 | 14.00 | 18.00 |
| Sodium laureth (2EO) sulfate | — | — | — | — | — |
| Cocoamidopropyl betaine | 2.00 | 2.00 | 2.00 | 2.00 | 2.00 |
| Cocodiethanolamide | — | — | — | — | — |
| Polyquaternium-6 | — | — | — | — | — |
| Polyquaternium-7 | — | — | — | — | — |
| Polyquaternium-10 | — | — | — | — | — |
| Polyquaternium-16 | — | — | — | — | — |
| Cationic guar gum | — | — | — | — | — |
| Distearyl dimonium chloride | 0.20 | 0.20 | 0.20 | 0.20 | 0.20 |
| Fragrance | ±1.50 | ±1.50 | ±1.50 | ±1.50 | ±1.50 |
| Color | ±0.10 | ±0.10 | ±0.10 | ±0.10 | ±0.10 |
| Preservative | ±1.00 | ±1.00 | ±1.00 | ±1.00 | ±1.00 |
| Behenyl alcohol | 1.00 | 1.00 | 1.00 | 1.50 | 2.00 |
| Dimethicone (60,000 cst) | 0.25 | 0.50 | 1.00 | 2.00 | 2.00 |
| pH modifier | ±1.00 | ±1.00 | ±1.00 | ±1.00 | ±1.00 |
| Viscosity modifier | ±1.00 | ±1.00 | ±1.00 | ±1.00 | ±1.00 |
| Water | 86.95 | 83.70 | 81.20 | 75.70 | 71.20 |

TABLE L

| Property | Ex. 26 | Ex. 27 | Ex. 28 | Ex. 29 | Ex. 30 |
|---|---|---|---|---|---|
| Stability | Yes | Yes | Yes | Yes | Yes |
| Pearlescence | Acceptable | Acceptable | Acceptable | Acceptable | High |
| Conditioning | 5 | 6 | 7 | 8 | 8.5 |

These compositions show stability and pearlesence.

Examples 31–35

General Method A may be used to make the compositions listed in Table M with the amounts of ingredients indicated. The compositions of Examples 31–35 may be evaluated for stability, pearlescence, and conditioning ability using the procedures listed above under General Examples B and C. The results are in Table N.

TABLE M

| Ingredient | Ex. 31 | Ex. 32 | Ex. 33 | Ex. 34 | Ex. 35 |
|---|---|---|---|---|---|
| Ammonium lauryl sulfate | 12.00 | 12.00 | 12.00 | 12.00 | 12.00 |
| Sodium laureth (2EO) sulfate | — | — | — | — | — |
| Cocoamidopropyl betaine | 3.00 | 4.00 | 0.50 | 3.00 | 0.25 |
| Cocodiethanolamide | — | — | — | — | — |
| Polyquaternium-6 | 0.25 | 0.25 | 0.25 | 0.25 | 0.25 |
| Polyquaternium-7 | — | — | — | — | — |
| Polyquaternium-10 | — | — | — | — | — |
| Polyquaternium-16 | — | — | — | — | — |
| Cationic guar gum | — | — | — | — | — |
| Distearyl dimonium chloride | — | — | — | — | — |
| Fragrance | ±1.50 | ±1.50 | ±1.50 | ±1.50 | ±1.50 |
| Color | ±0.10 | ±0.10 | ±0.10 | ±0.10 | ±0.10 |

TABLE M-continued

| Ingredient | Ex. 31 | Ex. 32 | Ex. 33 | Ex. 34 | Ex. 35 |
|---|---|---|---|---|---|
| Preservative | ±1.00 | ±1.00 | ±1.00 | ±1.00 | ±1.00 |
| Behenyl alcohol | 2.50 | 3.00 | 4.00 | 0.50 | 0.25 |
| Dimethicone (60,000 cst) | 2.50 | 2.50 | 3.50 | 4.00 | 3.00 |
| pH modifier | ±1.00 | ±1.00 | ±1.00 | ±1.00 | ±1.00 |
| Viscosity modifier | ±1.00 | ±1.00 | ±1.00 | ±1.00 | ±1.00 |
| Water | 75.15 | 73.65 | 75.15 | 75.65 | 79.65 |

TABLE N

| Property | Ex. 31 | Ex. 32 | Ex. 33 | Ex. 34 | Ex. 35 |
|---|---|---|---|---|---|
| Stability | Yes | Yes | Yes | Unstable | Unstable |
| Pearlescence | High | High | Very High | Acceptable | Light |
| Conditioning | 5 | 6 | 7 | 8 | 6.5 |

These compositions show pearlesence, but the lower amounts of behenyl alcohol do not provide the desired stability.

Examples 36–40

General Method A may be used to make the compositions listed in Table O with the amounts of ingredients indicated. The compositions of Examples 36–40 may be evaluated for stability, pearlescence, and conditioning ability using the procedures listed above under General Examples B and C. The results are in Table P.

TABLE O

| Ingredient | Ex. 36 | Ex. 37 | Ex. 38 | Ex. 39 | Ex. 40 |
|---|---|---|---|---|---|
| Ammonium lauryl sulfate | 12.00 | 12.00 | 12.00 | 12.00 | 12.00 |
| Sodium laureth (2EO) sulfate | — | — | — | — | — |
| Cocoamidopropyl betaine | 3.00 | 4.00 | 0.50 | 3.00 | 0.25 |
| Cocodiethanolamide | — | — | — | — | — |
| Polyquaternium-6 | — | — | — | — | — |
| Polyquaternium-7 | 0.25 | 0.25 | 0.25 | 0.25 | 0.25 |
| Polyquaternium-10 | — | — | — | — | — |
| Polyquaternium-16 | — | — | — | — | — |
| Cationic guar gum | — | — | — | — | — |
| Distearyl dimonium chloride | — | — | — | — | — |
| Fragrance | ±1.50 | ±1.50 | ±1.50 | ±1.50 | ±1.50 |
| Color | ±0.10 | ±0.10 | ±0.10 | ±0.10 | ±0.10 |
| Preservative | ±1.00 | ±1.00 | ±1.00 | ±1.00 | ±1.00 |
| Behenyl alcohol | 2.50 | 3.00 | 4.00 | 0.50 | 0.25 |
| Dimethicone (60,000 cst) | 2.50 | 2.50 | 3.50 | 4.00 | 3.00 |
| pH modifier | ±1.00 | ±1.00 | ±1.00 | ±1.00 | ±1.00 |
| Viscosity modifier | ±1.00 | ±1.00 | ±1.00 | ±1.00 | ±1.00 |
| Water | 75.15 | 73.65 | 75.15 | 75.65 | 79.65 |

TABLE P

| Property | Ex. 36 | Ex. 37 | Ex. 38 | Ex. 39 | Ex. 40 |
|---|---|---|---|---|---|
| Stability | Yes | Yes | Yes | Unstable | Unstable |
| Pearlescence | High | High | Very High | Acceptable | Light |
| Conditioning | 8.0 | 7.0 | 9.0 | 9.00 | 8.0 |

These compositions show pearlesence, but the lower amounts of behenyl alcohol do not provide the desired stability.

Examples 41–45

General Method A may be used to make the compositions listed in Table Q with the amounts of ingredients indicated. The compositions of Examples 41–45 may be evaluated for stability, pearlescence, and conditioning ability using the procedures listed above under General Examples B and C. The results are in Table R.

TABLE Q

| Ingredient | Ex. 41 | Ex. 42 | Ex. 43 | Ex. 44 | Ex. 45 |
|---|---|---|---|---|---|
| Ammonium lauryl sulfate | 12.00 | 12.00 | 12.00 | 12.00 | 12.00 |
| Sodium laureth (2EO) sulfate | — | — | — | — | — |
| Cocoamidopropyl betaine | 3.00 | 4.00 | 0.50 | 3.00 | 0.25 |
| Cocodiethanolamide | — | — | — | — | — |
| Polyquaternium-6 | — | — | — | — | — |
| Polyquaternium-7 | — | — | — | — | — |
| Polyquaternium-10 | 0.25 | 0.25 | 0.25 | 0.25 | 0.25 |
| Polyquaternium-16 | — | — | — | — | — |
| Cationic guar gum | — | — | — | — | — |
| Distearyl dimonium chloride | — | — | — | — | — |
| Fragrance | ±1.50 | ±1.50 | ±1.50 | ±1.50 | ±1.50 |
| Color | ±0.10 | ±0.10 | ±0.10 | ±0.10 | ±0.10 |
| Preservative | ±1.00 | ±1.00 | ±1.00 | ±1.00 | ±1.00 |
| Behenyl alcohol | 2.50 | 3.00 | 4.00 | 0.50 | 0.25 |
| Dimethicone (60,000 cst) | 2.50 | 2.50 | 3.50 | 4.00 | 3.00 |
| pH modifier | ±1.00 | ±1.00 | ±1.00 | ±1.00 | ±1.00 |
| Viscosity modifier | ±1.00 | ±1.00 | ±1.00 | ±1.00 | ±1.00 |
| Water | 75.15 | 73.65 | 75.15 | 75.65 | 79.65 |

TABLE R

| Property | Ex. 41 | Ex. 42 | Ex. 43 | Ex. 44 | Ex. 45 |
|---|---|---|---|---|---|
| Stability | Yes | Yes | Yes | Unstable | Unstable |
| Pearlescence | High | High | Very High | Acceptable | Light |
| Conditioning | 8.5 | 7.5 | 9.5 | 9.5 | 8.5 |

These compositions show pearlesence, but the lower amounts of behenyl alcohol do not provide the desired stability.

Examples 46–50

General Method A may be used to make the compositions listed in Table S with the amounts of ingredients indicated. The compositions of Examples 46–50 may be evaluated for stability, pearlescence, and conditioning ability using the procedures listed above under General Examples B and C. The results are in Table T.

TABLE S

| Ingredient | Ex. 46 | Ex. 47 | Ex. 48 | Ex. 49 | Ex. 50 |
|---|---|---|---|---|---|
| Ammonium lauryl sulfate | 12.00 | 12.00 | 12.00 | 12.00 | 12.00 |
| Sodium laureth (2EO) sulfate | — | — | — | — | — |
| Cocoamidopropyl betaine | 3.00 | 4.00 | 0.50 | 3.00 | 0.25 |
| Cocodiethanolamide | — | — | — | — | — |
| Polyquaternium-6 | — | — | — | — | — |
| Polyquaternium-7 | — | — | — | — | — |
| Polyquaternium-10 | — | — | — | — | — |
| Polyquaternium-16 | 0.25 | 0.25 | 0.25 | 0.25 | 0.25 |
| Cationic guar gum | — | — | — | — | — |
| Distearyl dimonium chloride | — | — | — | — | — |
| Fragrance | ±1.50 | ±1.50 | ±1.50 | ±1.50 | ±1.50 |
| Color | ±0.10 | ±0.10 | ±0.10 | ±0.10 | ±0.10 |
| Preservative | ±1.00 | ±1.00 | ±1.00 | ±1.00 | ±1.00 |
| Behenyl alcohol | 2.50 | 3.00 | 4.00 | 0.50 | 0.25 |
| Dimethicone (60,000 cst) | 2.50 | 2.50 | 3.50 | 4.00 | 3.00 |
| pH modifier | ±1.00 | ±1.00 | ±1.00 | ±1.00 | ±1.00 |
| Viscosity modifier | ±1.00 | ±1.00 | ±1.00 | ±1.00 | ±1.00 |
| Water | 75.15 | 73.65 | 75.15 | 75.65 | 79.65 |

TABLE T

| Property | Ex. 46 | Ex. 47 | Ex. 48 | Ex. 49 | Ex. 50 |
|---|---|---|---|---|---|
| Stability | Yes | Yes | Yes | Unstable | Unstable |
| Pearlescence | High | High | Very High | Acceptable | Light |
| Conditioning | 7.0 | 6.0 | 8.0 | 8.00 | 6.0 |

These compositions show pearlesence, but the lower amounts of behenyl alcohol do not provide the desired stability.

Examples 51–55

General Method A may be used to make the compositions listed in Table U with the amounts of ingredients indicated. The compositions of Examples 51–55 may be evaluated for stability, pearlescence, and conditioning ability using the procedures listed above under General Examples B and C. The results are in Table V.

TABLE U

| Ingredient | Ex. 51 | Ex. 52 | Ex. 53 | Ex. 54 | Ex. 55 |
|---|---|---|---|---|---|
| Ammonium lauryl sulfate | 12.00 | 12.00 | 12.00 | 12.00 | 12.00 |
| Sodium laureth (2EO) sulfate | — | — | — | — | — |
| Cocoamidopropyl betaine | 3.00 | 4.00 | 0.50 | 3.00 | 0.25 |
| Cocodiethanolamide | — | — | — | — | — |
| Polyquaternium-6 | — | — | — | — | — |
| Polyquaternium-7 | — | — | — | — | — |
| Polyquaternium-10 | — | — | — | — | — |
| Aculyn-33 | 2 | 2.5 | 3.00 | 3.5 | 4.00 |
| Cationic guar gum | 0.25 | 0.25 | 0.25 | 0.25 | 0.25 |
| Distearyl dimonium chloride | — | — | — | — | — |
| Fragrance | ±1.50 | ±1.50 | ±1.50 | ±1.50 | ±1.50 |
| Color | ±0.10 | ±0.10 | ±0.10 | ±0.10 | ±0.10 |
| Preservative | ±1.00 | ±1.00 | ±1.00 | ±1.00 | ±1.00 |
| Behenyl alcohol | 1.0 | 1.0 | 1.0 | 1.0 | 1.0 |
| Dimethicone (60,000 cst) | 2.50 | 2.50 | 3.50 | 4.00 | 3.00 |
| pH modifier | ±1.00 | ±1.00 | ±1.00 | ±1.00 | ±1.00 |
| Viscosity modifier | ±1.00 | ±1.00 | ±1.00 | ±1.00 | ±1.00 |
| Water | 75.15 | 73.65 | 75.15 | 75.65 | 79.65 |

TABLE V

| Property | Ex. 51 | Ex. 52 | Ex. 53 | Ex. 54 | Ex. 55 |
|---|---|---|---|---|---|
| Stability | Yes | Yes | Yes | Yes | Yes |
| Pearlescence | Acceptable | Acceptable | Acceptable | Acceptable | Acceptable |
| Conditioning | 7 | 7.0 | 8.0 | 9.0 | 7.5 |

These compositions show pearlesence and stability.

Examples 56–60

General Method A may be used to make the compositions listed in Table W with the amounts of ingredients indicated. The compositions of Examples 56–60 may be evaluated for stability, pearlescence, and conditioning ability using the procedures listed above under General Examples B and C. The results are in Table X.

TABLE W

| Ingredient | Ex. 56 | Ex. 57 | Ex. 58 | Ex. 59 | Ex. 60 |
|---|---|---|---|---|---|
| Ammonium lauryl sulfate | 12.00 | 12.00 | 12.00 | 12.00 | 12.00 |
| Sodium laureth (2EO) sulfate | — | — | — | — | — |
| Cocoamidopropyl betaine | 3.00 | 4.00 | 0.50 | 3.00 | 0.25 |
| Cocodiethanolamide | — | — | — | — | — |
| Polyquaternium-6 | — | — | — | — | — |
| Polyquaternium-7 | — | — | — | — | — |
| Polyquaternium-10 | — | — | — | — | — |
| Aculyn-33 | 2.0 | 2.5 | 3.0 | 3.5 | 3.5 |
| Cationic guar gum | 0.25 | 0.25 | 0.25 | 0.25 | 0.25 |
| Distearyl dimonium chloride | — | — | — | — | — |
| Fragrance | ±1.50 | ±1.50 | ±1.50 | ±1.50 | ±1.50 |
| Color | ±0.10 | ±0.10 | ±0.10 | ±0.10 | ±0.10 |
| Preservative | ±1.00 | ±1.00 | ±1.00 | ±1.00 | ±1.00 |
| Behenyl alcohol | 2.50 | 3.00 | 4.00 | 0.50 | 0.25 |
| Dimethicone (60,000 cst) | 2.50 | 2.50 | 3.50 | 4.00 | 3.00 |
| pH modifier | ±1.00 | ±1.00 | ±1.00 | ±1.00 | ±1.00 |
| Viscosity modifier | ±1.00 | ±1.00 | ±1.00 | ±1.00 | ±1.00 |
| Water | 75.15 | 73.65 | 75.15 | 75.65 | 79.65 |

TABLE X

| Property | Ex. 56 | Ex. 57 | Ex. 58 | Ex. 59 | Ex. 60 |
|---|---|---|---|---|---|
| Stability | Yes | Yes | Yes | Yes | Yes |
| Pearlescence | Acceptable | Acceptable | Acceptable | Acceptable | Acceptable |
| Conditioning | 7 | 7.0 | 8.0 | 9.0 | 7.5 |

These compositions show pearlesence and stability.

Examples 61–65

General Method A may be used to make the compositions listed in Table Y with the amounts of ingredients indicated. The compositions of Examples 61–65 may be evaluated for stability, pearlescence, and conditioning ability using the procedures listed above under General Examples B and C. The results are in Table Z.

TABLE Y

| Ingredient | Ex. 61 | Ex. 62 | Ex. 63 | Ex. 64 | Ex. 65 |
|---|---|---|---|---|---|
| Ammonium lauryl sulfate | 12.00 | 12.00 | 12.00 | 12.00 | 12.00 |
| Sodium laureth (2EO) sulfate | — | — | — | — | — |
| Cocoamidopropyl betaine | 3.00 | 4.00 | 0.50 | 3.00 | 0.25 |
| Cocodiethanolamide | — | — | — | — | — |
| Polyquaternium-6 | — | — | — | — | — |
| Polyquaternium-7 | — | — | — | — | — |
| Polyquaternium-10 | — | — | — | — | — |
| Aculyn-33 | 3.0 | 3.0 | 3.0 | 3.0 | 3.0 |
| Climbazole | 0.5 | 0.5 | 0.5 | 0.5 | 0.5 |
| Distearyl dimonium chloride | 0.25 | 0.25 | 0.25 | 0.25 | 0.25 |
| Fragrance | ±1.50 | ±1.50 | ±1.50 | ±1.50 | ±1.50 |
| Color | ±0.10 | ±0.10 | ±0.10 | ±0.10 | ±0.10 |
| Preservative | ±1.00 | ±1.00 | ±1.00 | ±1.00 | ±1.00 |
| Behenyl alcohol | 1.0 | 1.0 | 1.0 | 1.0 | 1.0 |
| Dimethicone (60,000 cst) | 2.50 | 2.50 | 3.50 | 4.00 | 3.00 |
| pH modifier | ±1.00 | ±1.00 | ±1.00 | ±1.00 | ±1.00 |
| Viscosity modifier | ±1.00 | ±1.00 | ±1.00 | ±1.00 | ±1.00 |
| Water | 75.15 | 73.65 | 75.15 | 75.65 | 79.65 |

TABLE Z

| Property | Ex. 61 | Ex. 62 | Ex. 63 | Ex. 64 | Ex. 65 |
|---|---|---|---|---|---|
| Stability | Yes | Yes | Yes | Yes | Yes |
| Pearlescence | Acceptable | Acceptable | Acceptable | Acceptable | Acceptable |
| Conditioning | 6.0 | 5.0 | 7.0 | 4.0 | 6.0 |

These compositions show pearlesence and stability.

Examples 66–70

General Method A may be used to make the compositions listed in Table AA with the amounts of ingredients indicated. The compositions of Examples 66–70 may be evaluated for stability, pearlescence, and conditioning ability using the procedures listed above under General Examples B and C. The results are in Table AB.

TABLE AA

| Ingredient | Ex. 66 | Ex. 67 | Ex. 68 | Ex. 69 | Ex. 70 |
|---|---|---|---|---|---|
| Ammonium lauryl sulfate | — | 8.00 | 10.00 | — | 14.00 |
| Sodium laureth (2EO) sulfate | 8.00 | — | — | 12.00 | — |
| Cocoamidopropyl betaine | 2.00 | — | — | 3.00 | — |
| Cocodiethanolamide | — | 2.00 | 2.00 | — | 2.00 |
| Polyquaternium-6 | 0.20 | 0.20 | 0.20 | 0.20 | 0.20 |
| Polyquaternium-7 | 0.20 | 0.20 | 0.20 | 0.20 | 0.20 |
| Polyquaternium-10 | 0.20 | 0.20 | 0.20 | 0.20 | 0.20 |
| Polyquaternium-16 | — | — | — | — | — |
| Cationic guar gum | — | — | — | — | — |
| Distearyl dimonium chloride | — | — | — | — | — |
| Fragrance | ±1.50 | ±1.50 | ±1.50 | ±1.50 | ±1.50 |
| Color | ±0.10 | ±0.10 | ±0.10 | ±0.10 | ±0.10 |
| Preservative | ±1.00 | ±1.00 | ±1.00 | ±1.00 | ±1.00 |
| Behenyl alcohol | 1.00 | 1.00 | 1.00 | 1.00 | 1.00 |
| Dimethicone (60,000 cst) | 1.00 | 1.00 | 1.00 | 1.00 | 1.00 |
| pH modifier | ±1.00 | ±1.00 | ±1.00 | ±1.00 | ±1.00 |
| Viscosity modifier | ±1.00 | ±1.00 | ±1.00 | ±1.00 | ±1.00 |
| Water | 86.95 | 83.95 | 81.95 | 77.95 | 73.95 |

TABLE AB

| Property | Ex. 66 | Ex. 67 | Ex. 68 | Ex. 69 | Ex. 70 |
|---|---|---|---|---|---|
| Stability | Yes | Yes | Yes | Yes | Yes |
| Pearlescence | Acceptable | Acceptable | Acceptable | Acceptable | Acceptable |
| Conditioning | 7 | 7 | 7 | 7 | 7 |

These compositions show pearlesence and stability.

Examples 71–75

General Method A may be used to make the compositions listed in Table AC with the amounts of ingredients indicated. The compositions of Examples 71–75 may be evaluated for stability, pearlescence, and conditioning ability using the procedures listed above under General Examples B and C. The results are in Table AD.

TABLE AC

| Ingredient | Ex. 71 | Ex. 72 | Ex. 73 | Ex. 74 | Ex. 75 |
|---|---|---|---|---|---|
| Ammonium lauryl sulfate | — | — | 14.00 | 14.00 | 7.50 |
| Sodium laureth (2EO) sulfate | 14.00 | 14.00 | — | — | 7.50 |
| Cocoamidopropyl betaine | 3.00 | — | 3.00 | — | 2.00 |
| Cocodiethanolamide | — | 3.00 | — | 3.00 | 1.00 |
| Polyquaternium-6 | 0.20 | 0.20 | 0.20 | 0.20 | 0.20 |
| Polyquaternium-7 | 0.20 | 0.20 | 0.20 | 0.20 | 0.20 |
| Polyquaternium-10 | 0.20 | 0.20 | 0.20 | 0.20 | 0.20 |
| Aculyn-33 | 2.5 | 2.5 | 2.5 | 2.5 | 2.5 |
| Fragrance | ±1.50 | ±1.50 | ±1.50 | ±1.50 | ±1.50 |
| Color | ±0.10 | ±0.10 | ±0.10 | ±0.10 | ±0.10 |
| Preservative | ±1.00 | ±1.00 | ±1.00 | ±1.00 | ±1.00 |
| Behenyl alcohol | 1.00 | 1.00 | 1.00 | 1.00 | 1.00 |
| Dimethicone (60,000 cst) | 1.00 | 2.00 | 3.00 | 3.5 | 4.00 |
| pH modifier | ±1.00 | ±1.00 | ±1.00 | ±1.00 | ±1.00 |
| Viscosity modifier | ±1.00 | ±1.00 | ±1.00 | ±1.00 | ±1.00 |
| Water | 75.80 | ? | ? | ? | ? |

TABLE AD

| Property | Ex. 71 | Ex. 72 | Ex. 73 | Ex. 74 | Ex. 75 |
|---|---|---|---|---|---|
| Stability | Yes | Yes | Yes | Yes | Yes |
| Pearlescence | Acceptable | Acceptable | Acceptable | Acceptable | Acceptable |
| Conditioning | 7 | 7.5 | 8.0 | 8.5 | 9.0 |

These compositions show pearlesence and stability.

Examples 76–80

General Method A may be used to make the compositions listed in Table AE with the amounts of ingredients indicated. The compositions of Examples 76–80 may be evaluated for stability, pearlescence, and conditioning ability using the procedures listed above under General Examples B and C. The results are in Table AF.

TABLE AE

| Ingredient | Ex. 76 | Ex. 77 | Ex. 78 | Ex. 79 | Ex. 80 |
|---|---|---|---|---|---|
| Ammonium lauryl sulfate | — | — | — | 12.00 | 14.00 |
| Sodium laureth (2EO) sulfate | 5.00 | 6.00 | 8.00 | — | — |
| Cocoamidopropyl betaine | 3.00 | — | 2.00 | 3.00 | — |
| Cocodiethanolamide | — | 4.00 | — | — | 2.00 |
| Polyquaternium-6 | 0.20 | — | — | — | — |
| Polyquaternium-7 | — | 0.20 | — | — | — |
| Polyquaternium-10 | — | — | 0.20 | — | — |
| Polyquaternium-16 | — | — | — | 0.20 | — |
| Cationic guar gum | — | — | — | — | 0.20 |
| Distearyl dimonium chloride | — | — | — | — | — |
| Fragrance | ±1.50 | ±1.50 | ±1.50 | ±1.50 | ±1.50 |
| Color | ±0.10 | ±0.10 | ±0.10 | ±0.10 | ±0.10 |
| Preservative | ±1.00 | ±1.00 | ±1.00 | ±1.00 | ±1.00 |
| Behenyl alcohol | 1.00 | 1.00 | 1.50 | 2.00 | 3.00 |
| Dimethicone (60,000 cst) | — | — | — | — | — |
| pH modifier | ±1.00 | ±1.00 | ±1.00 | ±1.00 | ±1.00 |
| Viscosity modifier | ±1.00 | ±1.00 | ±1.00 | ±1.00 | ±1.00 |
| Water | 87.20 | 85.20 | 85.20 | 80.20 | 79.20 |

TABLE AF

| Property | Ex. 76 | Ex. 77 | Ex. 78 | Ex. 79 | Ex. 80 |
|---|---|---|---|---|---|
| Stability | Yes | Yes | Yes | Yes | Yes |
| Pearlescence | Acceptable | Acceptable | Acceptable | Acceptable | High |
| Conditioning | 3 | 4 | 4.5 | 5.0 | 4.5 |

These compositions show pearlesence and stability.

Examples 81–85

General Method A may be used to make the compositions listed in Table AG with the amounts of ingredients indicated. The compositions of Examples 81–85 may be evaluated for stability, pearlescence, and conditioning ability using the procedures listed above under General Examples B and C. The results are in Table AH.

TABLE AG

| Ingredient | Ex. 81 | Ex. 82 | Ex. 83 | Ex. 84 | Ex. 85 |
|---|---|---|---|---|---|
| Ammonium lauryl sulfate | — | — | — | 12.00 | 14.00 |
| Sodium laureth (2EO) sulfate | 5.00 | 6.00 | 8.00 | — | — |
| Cocoamidopropyl betaine | 3.00 | — | 2.00 | 3.00 | — |
| Cocodiethanolamide | — | 4.00 | — | — | 2.00 |
| Polyquaternium-6 | 0.20 | — | — | — | — |
| Polyquaternium-7 | — | 0.20 | — | — | — |
| Polyquaternium-10 | — | — | 0.20 | — | — |
| Polyquaternium-16 | — | — | — | 0.20 | — |
| Cationic guar gum | — | — | — | — | 0.20 |
| Distearyl dimonium chloride | — | — | — | — | — |
| Fragrance | ±1.50 | ±1.50 | ±1.50 | ±1.50 | ±1.50 |
| Color | ±0.10 | ±0.10 | ±0.10 | ±0.10 | ±0.10 |
| Preservative | ±1.00 | ±1.00 | ±1.00 | ±1.00 | ±1.00 |
| Behenyl alcohol | 1.00 | 1.00 | 1.50 | 2.00 | 3.00 |
| Dimethicone (60,000 cst) | — | — | — | — | — |
| pH modifier | ±1.00 | ±1.00 | ±1.00 | ±1.00 | ±1.00 |
| Viscosity modifier | ±1.00 | ±1.00 | ±1.00 | ±1.00 | ±1.00 |
| Water | 87.20 | 85.20 | 85.20 | 80.20 | 79.20 |

TABLE AH

| Property | Ex. 81 | Ex. 82 | Ex. 83 | Ex. 84 | Ex. 85 |
|---|---|---|---|---|---|
| Stability | Yes | Yes | Yes | Yes | Yes |
| Pearlescence | Yes | Yes | Yes | Yes | Yes |
| Conditioning | 4.5 | 4.5 | 4.0 | 4.0 | 3.5 |

These compositions show pearlesence and stability.

Examples 86–90

General Method A may be used to make the compositions listed in Table AI with the amounts of ingredients indicated. The compositions of Examples 86–90 may be evaluated for stability, pearlescence, and conditioning ability using the procedures listed above under General Examples B and C. The results are in Table AJ.

TABLE AI

| Ingredient | Ex. 86 | Ex. 87 | Ex. 88 | Ex. 89 | Ex. 90 |
|---|---|---|---|---|---|
| Ammonium lauryl sulfate | — | — | — | 12.00 | 14.00 |
| Sodium laureth (2EO) sulfate | 5.00 | 6.00 | 8.00 | — | — |
| Cocoamidopropyl betaine | 3.00 | — | 2.00 | 3.00 | — |
| Cocodiethanolamide | — | 4.00 | — | — | 2.00 |
| Polyquaternium-6 | 0.20 | — | — | — | — |
| Polyquaternium-7 | — | 0.20 | — | — | — |
| Polyquaternium-10 | — | — | 0.20 | — | — |
| Polyquaternium-16 | — | — | — | 0.20 | — |
| Cationic guar gum | — | — | — | — | 0.20 |
| Distearyl dimonium chloride | — | — | — | — | — |
| Fragrance | ±1.50 | ±1.50 | ±1.50 | ±1.50 | ±1.50 |
| Color | ±0.10 | ±0.10 | ±0.10 | ±0.10 | ±0.10 |
| Preservative | ±1.00 | ±1.00 | ±1.00 | ±1.00 | ±1.00 |
| Behenyl alcohol | — | — | — | — | — |
| Dimethicone (60,000 cst) | 2.00 | 2.00 | 2.00 | 2.00 | 2.00 |
| pH modifier | ±1.00 | ±1.00 | ±1.00 | ±1.00 | ±1.00 |
| Viscosity modifier | ±1.00 | ±1.00 | ±1.00 | ±1.00 | ±1.00 |
| Water | 87.20 | 85.20 | 85.20 | 80.20 | 79.20 |

TABLE AJ

| Property | Ex. 86 | Ex. 87 | Ex. 88 | Ex. 89 | Ex. 90 |
|---|---|---|---|---|---|
| Stability | No | No | No | No | No |
| Pearlescence | No | No | No | No | No |
| Conditioning | 5.5 | 7.5 | 8.0 | 6.0 | 6.0 |

These compositions do not show either pearlesence or stability.

Examples 91–95

General Method A may be used to make the compositions listed in Table AK with the amounts of ingredients indicated. The compositions of Examples 91–95 may be evaluated for stability, pearlescence, and conditioning ability using the procedures listed above under General Examples B and C. The results are in Table AL.

TABLE AK

| Ingredient | Ex. 91 | Ex. 92 | Ex. 93 | Ex. 94 | Ex. 95 |
|---|---|---|---|---|---|
| Ammonium lauryl sulfate | — | — | — | 12.00 | 14.00 |
| Sodium laureth (2EO) sulfate | 5.00 | 6.00 | 8.00 | — | — |
| Cocoamidopropyl betaine | 3.00 | — | 2.00 | 3.00 | — |
| Cocodiethanolamide | — | 4.00 | — | — | 2.00 |
| Polyquaternium-6 | 0.20 | — | — | — | — |
| Polyquaternium-7 | — | 0.20 | — | — | — |
| Polyquaternium-10 | — | — | 0.20 | — | — |
| Polyquaternium-16 | — | — | — | 0.20 | — |
| Cationic guar gum | — | — | — | — | 0.20 |
| Distearyl dimonium chloride | — | — | — | — | — |
| Fragrance | ±1.50 | ±1.50 | ±1.50 | ±1.50 | ±1.50 |
| Color | ±0.10 | ±0.10 | ±0.10 | ±0.10 | ±0.10 |
| Preservative | ±1.00 | ±1.00 | ±1.00 | ±1.00 | ±1.00 |
| Behenyl alcohol | — | — | — | — | — |
| Dimethicone (60,000 cst) | — | — | — | — | — |
| pH modifier | ±1.00 | ±1.00 | ±1.00 | ±1.00 | ±1.00 |
| Viscosity modifier | ±1.00 | ±1.00 | ±1.00 | ±1.00 | ±1.00 |
| Water | 87.20 | 85.20 | 85.20 | 80.20 | 79.20 |

TABLE AL

| Property | Ex. 91 | Ex. 92 | Ex. 93 | Ex. 94 | Ex. 95 |
|---|---|---|---|---|---|
| Stability | Yes | Yes | Yes | Yes | Yes |
| Pearlescence | None | None | None | None | None |
| Conditioning | 3.5 | 5.5 | 6.0 | 4.0 | 4.0 |

These compositions do not show pearlesence. They are stable, but they are not conditioning formulations. The absence of silicones makes it easier to achieve stable compositions.

Examples 96–100

General Method A may be used to make the compositions listed in Table AM with the amounts of ingredients indicated. The compositions of Examples 96–100 may be evaluated for stability, pearlescence, and conditioning ability using the procedures listed above under General Examples B and C. The results are in Table AN.

TABLE AM

| Ingredient | Ex. 96 | Ex. 97 | Ex. 98 | Ex. 99 | Ex. 100 |
|---|---|---|---|---|---|
| Ammonium lauryl sulfate | — | — | — | 12.00 | 14.00 |
| Sodium laureth (2EO) sulfate | 10.00 | 10.00 | 12.00 | — | — |
| Cocoamidopropyl betaine | 2.00 | — | 3.00 | 3.00 | — |
| Cocodiethanolamide | — | 3.00 | — | — | 2.00 |
| Polyquaternium-6 | — | — | — | — | — |
| Polyquaternium-7 | 0.20 | 0.20 | 0.20 | 0.20 | 0.20 |
| Polyquaternium-10 | 0.20 | 0.20 | 0.20 | 0.20 | 0.20 |
| Polyquaternium-16 | — | — | — | — | — |
| Cationic guar gum | — | — | — | — | — |
| Distearyl dimonium chloride | — | — | — | — | — |
| Fragrance | ±1.50 | ±1.50 | ±1.50 | ±1.50 | ±1.50 |
| Color | ±0.10 | ±0.10 | ±0.10 | ±0.10 | ±0.10 |
| Preservative | ±1.00 | ±1.00 | ±1.00 | ±1.00 | ±1.00 |
| Behenyl alcohol | 1.00 | 1.00 | 1.00 | 1.00 | 1.00 |
| Dimethicone (60,000 cst) | 1.00 | 1.00 | 2.00 | 3.00 | 3.00 |
| Acrylates Copolymer | — | 1.60 | 1.60 | — | 1.60 |
| pH modifier | ±1.00 | ±1.00 | ±1.00 | ±1.00 | ±1.00 |
| Viscosity modifier | ±1.00 | ±1.00 | ±1.00 | ±1.00 | ±1.00 |
| Water | 81.00 | 79.40 | 75.40 | 76.00 | 73.40 |

TABLE AN

| Property | Ex. 96 | Ex. 97 | Ex. 98 | Ex. 99 | Ex. 100 |
|---|---|---|---|---|---|
| Stability | Yes | Yes | Yes | No | No |
| Pearlescence | Yes | Yes | Yes | Yes | Yes |
| Conditioning | 5.5 | 5.5 | 7.0 | 8.0 | 8.0 |

These examples show pearlized compositions. The differences in stability show that the amount of behenyl alcohol and acrylates copolymer must be increased if higher levels of silicone are used.

What is claimed is:

1. A pearlized cleansing composition for personal care comprising:

(a) 4.00–30.00 weight % of an anionic material selected from the group consisting of water soluble lipophilic sulfates and sulfonates having 8 to 22 carbon atoms;

(b) 0.25–4.0 weight % behenyl alcohol;

(c) 0–10.00 weight % of a non-ionic material selected from the group consisting of a higher fatty alkanolamide having 8–22 carbons;

(d) 0–10.00 weight % of an amphoteric material selected from the group consisting of derivatives of aliphatic quaternary ammonium, phosphonium or sulfonium compounds in which the aliphatic radicals can be straight chain or branched, and wherein one of the aliphatic substituents contains from 8–22 carbons and one contains an anionic water-solubilizing group selected from the group consisting of carboxyl, sulfonate, sulfate, phosphate and phosphonate; C8–C18 alkyl betaines; C8–C18 sulfobetaines; C8–C18 alkyl amphoacetates; and C8–C18 alkyl amphopropionates;

(e) optionally a cationic material which is a cationic surface active fiber conditioning agent selected from the group consisting of (i) 0–5.0 weight % of one or more quaternary ammonium salts of formula:

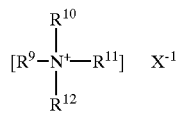

wherein $R^9$ is a lower alkyl having 1–4 carbons; $R^{10}$ and $R^{11}$ may be the same or different and are each selected from the group of higher alkyls having 10–40 carbons; $R^{12}$ is selected from the groups defined for $R^9$ and $R^{10}$; $X^-$ is a salt forming anion selected from the group consisting of a halide, lower (C1–C3) alkylsulfates, lower (C1–C3) carboxylic acid radicals, and citrate; and (ii) 0.0–2.0 weight % water soluble cationic cellulosic polymers selected from the group consisting of hydroxy alkyl celluloses, alkyl hydroxy alkyl celluloses, and galactomannan gums;

(f) 0.1–10 weight % of a silicone selected from the group consisting of water insoluble organosilicone compounds selected from the group consisting of:

(i) dimethicones, dimethicone derivatives and mixtures of the foregoing having a viscosity in the range of 5–100,000 centipoise (cps) and which are of Formula I:

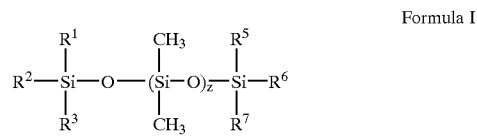

wherein $R^1$, $R^2$, $R^3$, $R^5$, $R^6$, and $R^7$ may be the same or different and are each independently selected from the group consisting of alkyls of 1–6 carbons and z is selected so that the viscosity of 5–100,000 is achieved; and (ii) aminosilicones of Formula II

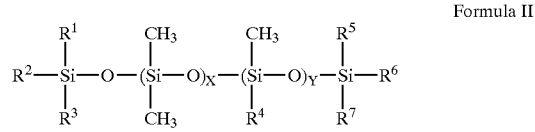

wherein $R^1$, $R^2$, $R^3$, $R^5$, $R^6$, and $R^7$ may be the same or different and are each independently selected from the group consisting of are alkyls of 1–6 carbons; and $R^4$ is $R^8$—NH—$CH_2CH_2$—$NH_2$, $R^8$ is an alkylene of 3–6 carbons;

x=is an average value and is a number in the range of 500–10,000; and y=is an average value and is a number in the range of 1–10;

(iii) mixtures of (f)(i) and (f)(ii);

(g) optionally, one or more members selected from the group consisting of an effective amount of a pH modifying agent; an effective amount of a viscosity modifying agent; an effective amount of a preservative; fragrance; and a coloring agent; and (h) the remainder water; provided that a sufficient amount of behenyl alcohol or behenyl alcohol in combination with an additional suspending agent is used to stabilize the composition.

2. A composition according to claim 1 wherein the anionic material has 10 to 18 carbon atoms.

3. A composition according to claim 1 wherein the anionic material is selected from the group consisting of ammonium lauryl sulfate, sodium lauryl diethoxy sulfate, ammonium lauryl triethoxy sulfate, sodium alpha C16 olefin sulfonate, sodium C14 paraffin sulfonate, sodium coco monoglyceride sulfate, triethanolamine cetyl sulfate and dimethylamine myristyl sulfate.

4. A composition according to claim 1 wherein the anionic material is selected from the group consisting of lauryl sulfate, lauryl diethoxy sulfate and lauryl triethoxy sulfate.

5. A composition according to claim 1 comprising 4–30 weight % of an anionic material itself comprising one or more of ammonium lauryl sulfate and sodium laureth (with 2 moles ethylene oxide) sulfate.

6. A composition according to claim 1 comprising 0.10–10.00 weight % of a non-ionic material selected from the group consisting of cocodiethanolamide, cocoethanolamide, cocoamidopropyl dimethylamine, cocoamine, cocoamine oxide, and cocoaminopropionic acid.

7. A composition according to claim 1 comprising 0.05–10.00 weight % of an amphoteric material having a formula of

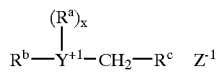

wherein $R^a$ is a C1–3 alkyl or monohydroxy alkyl; $R^b$ is a C8–18 alkyl, alkenyl or hydroxy alkyl radical with 0–10 ethylene oxide moieties and 0–1 glyceryl moiety; $R^c$ is a C1–4 alkylene or hydroxyalkylene, x is 1 when Y is a sulfur atom and X is 2 when Y is a nitrogen or phosphorous atom, Z is a radical selected from the group consisting of carboxylate, sulfonate, sulfate, phosphonate, and phosphate groups.

8. A composition according to claim 1 comprising 0.05–10.00 weight % of an amphoteric material selected from the group consisting of
  4-[N,N-di(2-hydroxyethyl)-N-octadecylammonio]-butane-1-carboxylate;
  5-[S-3-hydroxypropyl-S-hexadecylsulfonio]-3-hydroxypentae-1-sulfate;
  3-[P,P-diethyl-P-3,6,9-trioxatetradexocylphosphonio-]2-hydroxypropane-1-phosphate;
  3-[N,N-dipropyl-N-3-dodecoxy-2-hydroxypropylammonio]-propane-1-phosphonate;
  3-[N,N-di methyl-N-hexadecylammonio]-propane-1-sulfonate;
  4-[N,N-di (2-hydroxyethyl)-N-(2-hydroxydodecyl) ammonio]-butane-1-carbonate;
  3-[S-ethyl-S-(3-dodecoxy-2-hydroxypropyl)sulfonio]-propane-1-phosphate;
  3-[P,P-dimethyl-P-dodecylphosphonio]-propane-1-phosphonate; and
  5-[N,N-di(3-hydroxypropyl)-N-hexadecylammonio]-32-hydroxypentane-1-sulfate.

9. A composition according to claim 1 comprising 0.05–10.00 weight % of an amphoteric material selected from the group consisting of betaines selected from the group consisting of cocodimethyl carboxymethyl betaine, lauryl dimethyl carboxymethyl betaine, dlauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl)-carboxymethyl betaine, oleyl dimethyl gamma-carboxypropyl betaine, and lauryl bis-(2-hlydroxypropyl)alpha-carboxyethyl betaine.

10. A composition according to claim 1 comprising 0.05–10.00 weight % of an amphoteric material selected from the group consisting of cocoamidopropyl betaine, cocobetaine, cocosultaine, especially when one or more of non-ionic and zwitterionic materials can be used and where the total of non-ionic and zwitterionic material are in the range of 5–10 weight %.

11. A composition according to claim 1 comprising 0.05–10.00 weight % of an amphoteric material selected from the group consisting of C8–18 alkyl betaines, C8–18 alkyl sulfobetaines, C8–18 alkyl amphoacetates and C8–18 alkyl propionates.

12. A composition according to claim 1 comprising 0.05–10.00 weight % of an amphoteric material selected from the group consisting of betaines and sulfobetaines of formula

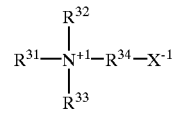

where $R^{31}$=C8–C22 alkyl, $R^{35}$ CO— (where $R^{35}$=C8–C22), $R^{36}$—C(O)—NH$_2$—(CH$_2$)$_3$— (where $R^{36}$=C8–C22);
  $R^{32}$=C1–C4 alkyl;
  $R^{33}$=C1–C4 alkyl;
  $R^{34}$=C1–C4 alkyl;
and $X^{-1}$=is selected from the group consisting of COO$^{-1}$; OSO$_3^{-1}$; CH$_3$CH$_2$COO$^{-1}$.

13. A composition according to claim 1 comprising 0.05–5.0 weight % of a cationic material selected from quaternary ammonium salts having the formula

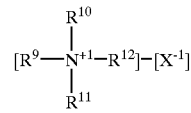

wherein $R^9$ is C1–C4 alky, $R^{10}$ and $R^{11}$ may be the same or different and are each selected from C10–C40 alkyls, $R^{12}$ is selected from the groups described for $R^9$ and $R^{10}$, and $X^-$ is a salt forming anion selected from the group consisting of halides, C1–C3 alkylsulfates, C1–C3 carboxylic acid radicals, and citrate.

14. A composition according to claim 13 wherein for the quaternary ammonium salts, $R^9$ is C1–C2 alkyl and $R^{10}$ and $R^{11}$ are selected from the group consisting of C10–C22 alkyls.

15. A composition according to claim 13 comprising 0.2–0.5 weight % of the quaternary ammonium salts.

16. A composition according to claim 13 wherein the cationic material is selected from the group consisting of tricetyl methyl ammonium chloride, distearyl dimethyl ammonium chloride, dilauryl dimethyl ammonium bromide, stearyl cetyl dimethyl ammonium chloride, trimyristyl ethyl ammonium bromide and trilauryl ethyl ammonium chloride.

17. A composition according to claim 1 comprising 0.05–0.4 weight % of the water soluble cellulosic polymers.

18. A composition according to claim 1 wherein the cationic material is selected from the group consisting of hydroxy alkyl celluloses and alkyl hydroxy alkyl celluloses.

19. A composition according to claim 1 wherein the cationic material is selected from the group consisting of guar gum and hydroxy alkylated guar gum.

20. A composition according to claim 1 which comprises 0.25–5.0 weight % of the silicone.

21. A composition according to claim 20 wherein the silicone is selected from the group consisting of dimethicones, aminosilicones and dimethiconols.

22. A composition according to claim 21 wherein the silicone has a viscosity in the range of 30,000–100,000 centistokes.

23. A composition according to claim 1 which is a shampoo.

24. A composition according to claim 1 comprising 7–20 weight % of the anionic marterial; and 0.25–4 weight % of a silicone which is a dispersed, insoluble, non-volatile silicone.

25. A composition according to claim 1 which is a body wash.

* * * * *